United States Patent [19]

Whitehouse et al.

[11] Patent Number: 5,425,637
[45] Date of Patent: Jun. 20, 1995

[54] METHOD AND APPARATUS FOR PREVENTING A BACK FLOW OF ORAL CONTAMINANTS IN A LOW VOLUME SUCTION LINE OF A DENTAL SALIVA EJECTOR

[75] Inventors: Ronald L. S. Whitehouse; Connie Watson, both of Edmonton, Canada

[73] Assignee: 601976 Alebrta Ltd., Edmonton, Canada

[21] Appl. No.: 220,550

[22] Filed: Mar. 31, 1994

[51] Int. Cl.⁶ ............................................. A61C 17/06
[52] U.S. Cl. ....................................... 433/95; 433/96
[58] Field of Search ..................... 433/91, 93, 94, 95, 433/96; 604/119

[56] References Cited

U.S. PATENT DOCUMENTS

| | | | |
|---|---|---|---|
| 1,222,267 | 4/1917 | Cosad | 433/91 |
| 1,388,312 | 8/1921 | Seeger | 433/96 |
| 1,930,196 | 10/1933 | Fisher | 433/94 |
| 3,453,735 | 7/1969 | Burt | 433/96 |
| 3,455,324 | 6/1969 | Bieri et al. | 137/216 |
| 3,516,160 | 6/1970 | Leffler | 433/95 |
| 3,881,254 | 5/1975 | Epstein | 433/96 |
| 4,221,220 | 9/1980 | Hansen | 433/95 |
| 4,417,874 | 11/1983 | Andersson et al. | 433/96 |
| 5,080,587 | 1/1992 | Miyao | 433/91 |
| 5,094,616 | 3/1992 | Levenson | 433/91 |
| 5,123,840 | 6/1992 | Nates | 433/91 |
| 5,195,952 | 3/1993 | Solnit et al. | 433/91 |

FOREIGN PATENT DOCUMENTS 2058576  4/1981  United Kingdom .................. 433/95

OTHER PUBLICATIONS

Article published in The Journal of The American Dental Association vol. 124 Apr. 1993 entitled Possibility of Cross-Contamination Between Dental Patients By Means Of The Saliva Ejector by C. M. Watson, R. D. H.: R. L. S. Whitehouse, PH.D.

*Primary Examiner*—Cary E. O'Connor
*Attorney, Agent, or Firm*—Anthony R. Lambert

[57] ABSTRACT

A method of preventing a back flow of oral contaminants in a low volume suction line of a dental saliva ejector is described. This method consists of the single step of placing a vacuum release aperture through a tubular sidewall of a saliva ejector tip. The aperture is spaced from a mouthpiece of the saliva ejector tip such that when the mouthpiece is inserted into a patient's mouth, the patient's mouth will not block the aperture.

2 Claims, 1 Drawing Sheet

METHOD AND APPARATUS FOR PREVENTING A BACK FLOW OF ORAL CONTAMINANTS IN A LOW VOLUME SUCTION LINE OF A DENTAL SALIVA EJECTOR

The present invention relates to a method and apparatus for preventing a back flow of oral contaminants in a low volume suction line of a dental saliva ejector.

BACKGROUND OF THE INVENTION

A saliva ejector is an apparatus which includes a suction line and a saliva ejector tip. The saliva ejector tip is disposable. It is inserted into the patient's mouth for the purpose of drawing away excess fluids through the suction line. In the April 1993 edition of the Journal of the American Dental Association, Watson and Whitehouse published a paper entitled "Possibility of Cross-contamination between Dental Patients by means of the Saliva Ejector". This paper documented that, when a patient closes his or her lips around the saliva ejector tip, a higher vacuum can be temporarily created in the mouth than in the suction line and a back flow of fluid containing oral contaminants into the mouth can occur.

Prior to the study by Watson and Whitehouse it had been felt that disposal and replacement of the saliva ejector tip was sufficient protection for the patient. The study clearly showed the presence of alpha-haemolytic organisms, characteristic of oral flora, in the suction line after use. This raises the possibility of a cross-contamination occurring between patients, and demonstrates the need to re-evaluate sanitation and hygienic practises in dental offices.

SUMMARY OF THE INVENTION

What is required is a method and apparatus for preventing a back flow of oral contaminants in a low volume suction line of a dental saliva ejector.

According to one aspect of the present invention there is provided a method of preventing a back flow of oral contaminants in a low volume suction line of a dental saliva ejector. This method consists of the single step of placing a vacuum release aperture through a tubular sidewall of a saliva ejector tip. The aperture is spaced from a mouthpiece of the saliva ejector tip such that when the mouthpiece is inserted into a patient's mouth, the patient's mouth will not block the aperture.

With the method, as described above, a higher level of vacuum cannot develop in the patients mouth as the vacuum is released by air from the room being drawn through the vacuum release aperture.

According to another aspect of the present invention there is provided a saliva ejector tip which includes a tubular body having a first end, a second end, and a tubular sidewall extending between the first end and the second end. A mouthpiece is provided at the second end. A vacuum release aperture extends through the tubular sidewall. The aperture is spaced from the mouthpiece such that when the mouthpiece is inserted into a patient's mouth, the patient's mouth will not block the aperture.

Although beneficial results may be obtained through the use of the saliva ejector tip, as described above, the saliva ejector tip is more readily maintained in the patient's mouth when it can be bent and will maintain the bend. This is accomplished at present by making the saliva ejector tip out of flexible tubing and placing a wire in the sidewall of the saliva ejector tip to assist in maintaining the bent position. Considering that the saliva ejector tip is intended to be disposable, this form of saliva ejector tip is comparatively expensive. Even more beneficial results may be obtained when the tubular body has at least one accordion-style flex joint. The tubular body is bent about the flex joint.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
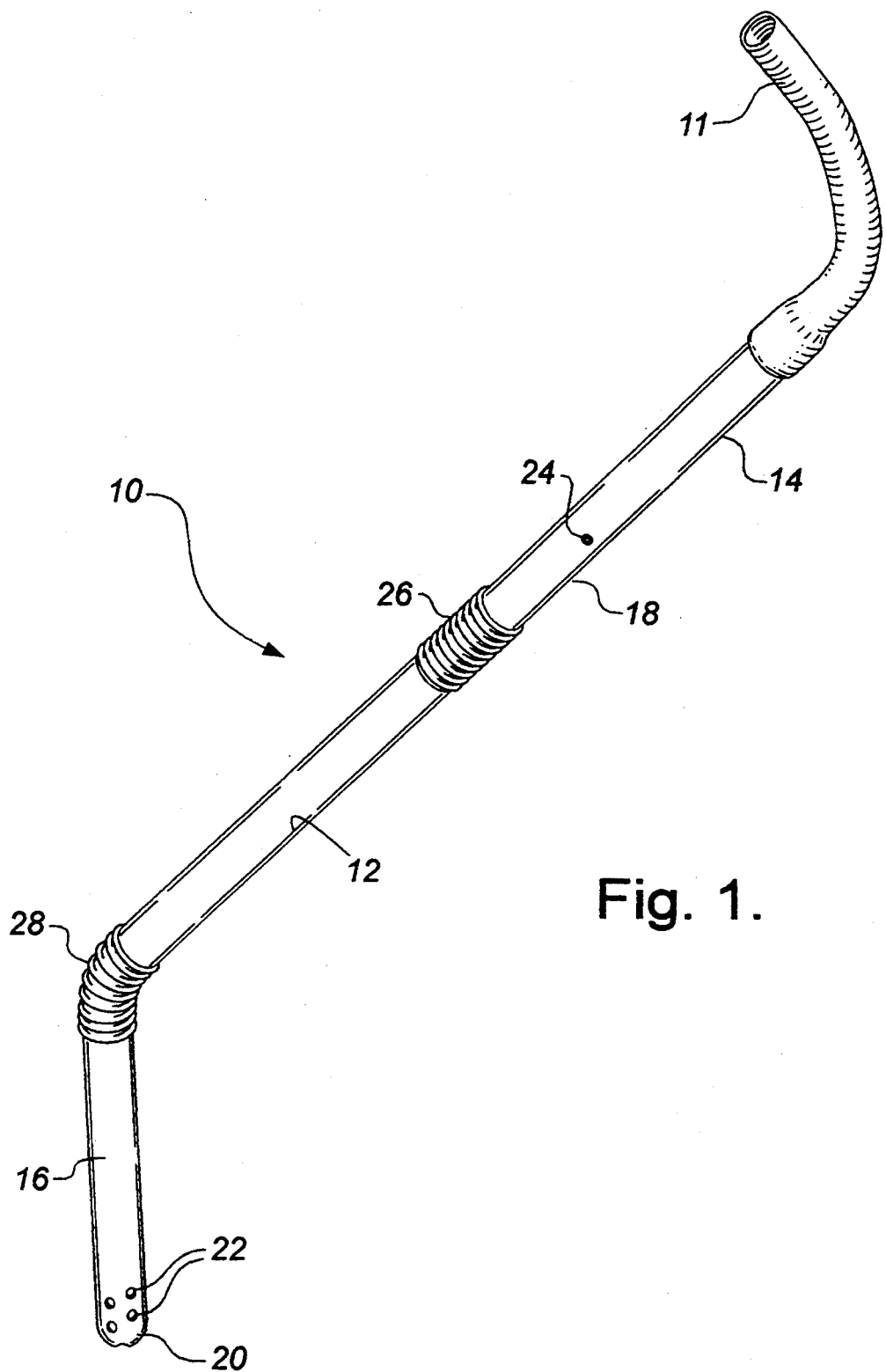
FIG. 1 is a side elevation view of a saliva ejector tip constructed in accordance with the teachings of the present invention.

The method of preventing a back flow of oral contaminants in a low volume suction line 11 of a dental saliva ejector consists of a single step. This step involves a modification of a saliva ejector tip 10 as will hereinafter be described.

The preferred embodiment, a saliva ejector tip generally identified by reference numeral 10, will now be described with reference to FIG. 1. Saliva ejector tip 10 includes a tubular body 12 having a first end 14, a second end 16, and a tubular sidewall 18 which extends between first end 14 and second end 16 defining a central passage 19. First end 14 is adapted for attachment by friction fit insertion into a suction line. A mouthpiece 20 is provided at second end 16. As is apparent from a review of FIG. 1, mouthpiece 20 need not be elaborate. In this case, it merely consists of a plurality of small holes 22. A vacuum release aperture 24 extends through tubular sidewall 18. Aperture 24 is spaced from mouthpiece 20. This is to ensure that when mouthpiece 20 is inserted into a patient's mouth (not shown), the patient's mouth will not block aperture 24. Tubular body 12 has two accordion-style flex joints 26 and 28.

The method of use of saliva ejector tip 10 will now be described with reference to FIG. 1. Prior to insertion into the patient's mouth, tubular body 12 is bent to a desired position about flex joints 26 and 28. Mouthpiece 20 is then placed into the patient's mouth. If a vacuum should start to form in the patients mouth, room air is drawn into saliva ejector tip 10 through aperture 24. As previously described, aperture 24 is spaced from mouthpiece 20 so that the patient's mouth will not block aperture 24.

It will be apparent to one skilled in that art that with the method and apparatus, as described above, a vacuum cannot develop in the patients mouth. The vacuum is released by an inflow of air being drawn through aperture 24. It will also be apparent to one skilled in the art that modifications may be made to the illustrated embodiment without departing from the spirit and scope of the invention as defined by the Claims.

The embodiments of the invention in which an exclusive property or privilege is claimed are as follows:

1. A method of preventing a back flow of oral contaminants in a suction line of a dental saliva ejector, comprising the steps of:
   placing onto the suction line a disposable saliva ejector tip having:
   a. a disposable tubular body having a first end, a second end, and a tubular sidewall extending between the first end and the second end thereby defining a single central passage;

b. a mouthpiece at the second end; and c. at least one unregulated vacuum release aperture through the tubular sidewall in direct communication with the single central passage, the aperture being spaced from the mouthpiece such that when the mouthpiece is inserted into a patient's mouth, the patient's mouth will not block the aperture; and taking preventative measures to ensure that the vacuum release aperture does not become blocked during use.

2. In combination:

a low volume dental office suction line; and a saliva ejector tip, comprising:

a. a disposable tubular body having a first end, a second end, and a tubular sidewall extending between the first end and the second end thereby defining a single central passage;

b. a mouthpiece at the second end; and c. at least one unregulated vacuum release aperture through the tubular sidewall in direct communication with the single central passage, the aperture being spaced from the mouthpiece such that when the mouthpiece is inserted into a patient's mouth, the patient's mouth will not block the aperture.

* * * * *